(12) United States Patent
Lee et al.

(10) Patent No.: US 10,589,115 B2
(45) Date of Patent: Mar. 17, 2020

(54) INNER EAR THERAPY DEVICE AND METHOD FOR OPERATING INNER EAR THERAPY DEVICE

(71) Applicant: YONSEI UNIVERSITY WONJU INDUSTRY-ACADEMIC COOPERATION FOUNDATION, Wonju-si (KR)

(72) Inventors: Yong Heum Lee, Wonju-si (KR); Na Ra Lee, Gimhae-si (KR)

(73) Assignee: YONSEI UNIVERSITY WONJU INDUSTRY-ACADEMIC COOPERATION FOUNDATION, Wonju-si (KR)

( * ) Notice: Subject to any disclaimer, the term of this patent is extended or adjusted under 35 U.S.C. 154(b) by 317 days.

(21) Appl. No.: 15/563,984

(22) PCT Filed: Apr. 7, 2016

(86) PCT No.: PCT/KR2016/003651
§ 371 (c)(1),
(2) Date: Oct. 3, 2017

(87) PCT Pub. No.: WO2016/163776
PCT Pub. Date: Oct. 13, 2016

(65) Prior Publication Data
US 2018/0133497 A1  May 17, 2018

(30) Foreign Application Priority Data
Apr. 7, 2015  (KR) .................. 10-2015-0049159

(51) Int. Cl.
*A61N 2/00* (2006.01)
*A61F 11/00* (2006.01)
(Continued)

(52) U.S. Cl.
CPC .............. *A61N 2/002* (2013.01); *A61F 11/00* (2013.01); *A61N 5/0603* (2013.01);
(Continued)

(58) Field of Classification Search
CPC ...... A61N 2/002; A61N 2/004; A61N 5/0603; A61N 5/0624; A61N 2005/0605; A61F 11/00
(Continued)

(56) References Cited

U.S. PATENT DOCUMENTS

2004/0073278 A1  4/2004  Pachys
2012/0203130 A1  8/2012  Bernhard

FOREIGN PATENT DOCUMENTS

KR         200254237      11/2001
KR       1020110079162      7/2011
(Continued)

OTHER PUBLICATIONS

International Search Report—PCT/KR2016/003651 dated Jul. 5, 2016.

*Primary Examiner* — John P Lacyk
(74) *Attorney, Agent, or Firm* — Cantor Colburn LLP

(57) ABSTRACT

An inner ear therapy device includes a magnetic field generation unit configured to generate a magnetic field toward the inner ear of a user, multiple light sources configured to irradiate multiple lights having different wavelengths toward the inner ear, and a control unit configured to control operations of the magnetic field generation unit and the multiple light sources.

19 Claims, 10 Drawing Sheets

(51) Int. Cl.
*A61N 5/06* (2006.01)
*A61N 2/02* (2006.01)

(52) U.S. Cl.
CPC .............. *A61N 5/0624* (2013.01); *A61N 2/02* (2013.01); *A61N 2005/0605* (2013.01); *A61N 2005/0626* (2013.01); *A61N 2005/0647* (2013.01); *A61N 2005/0651* (2013.01); *A61N 2005/0663* (2013.01)

(58) Field of Classification Search
USPC .................................................. 600/9–15, 25
See application file for complete search history.

(56) References Cited

FOREIGN PATENT DOCUMENTS

| | | |
|---|---|---|
| KR | 1020120115739 | 10/2012 |
| KR | 1020130084937 | 7/2013 |
| KR | 101431201 | 8/2014 |
| KR | 1020140107768 | 9/2014 |

512　　511

514　513　516　517
　515

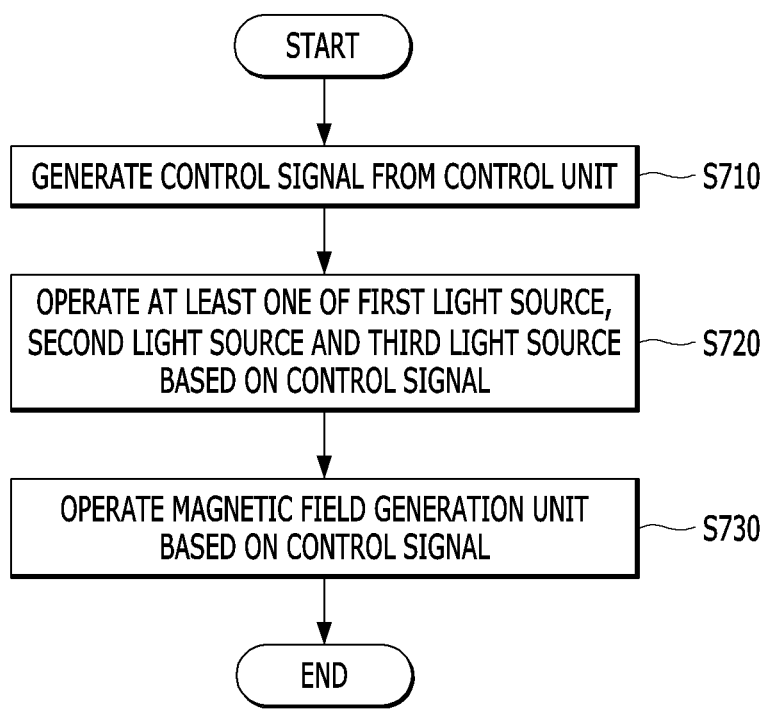

INNER EAR THERAPY DEVICE AND METHOD FOR OPERATING INNER EAR THERAPY DEVICE

TECHNICAL FIELD

The present disclosure relates to an inner ear therapy device that generates lights and a magnetic field and a method for operating the inner ear therapy device.

BACKGROUND

Middle ear infections typically occur when the middle ear is infected with bacteria or viruses and may be caused by various reasons such as a cold or allergies and family history, and when effusion turns into purulence so as to increase the pressure, the purulence ruptures the eardrum and then flows out to the ear canal. If the eardrum is ruptured and purulent secretion flows out as such, the effusion discharged through the ruptured eardrum becomes hard. Therefore, if the ruptured eardrum is not regenerated, hearing loss occurs.

In general, a therapy device used for treating middle ear infections, such as a far infrared ray therapy apparatus, is configured to treat an infection by irradiating a light of a specific wavelength range from the outside of the ear. A light irradiator used in this case mainly uses a single light source such as far infrared light. However, since light sources different in wavelength range have different effects, a light irradiator available for use in various wavelength ranges is needed.

Further, the conventional middle ear infection therapy device has been limited in stimulating or treating the deep inside of the ear since a light is irradiated from the outside of the ear. Furthermore, a user needs to continuously grip the middle ear infection therapy device with his/her hand, which causes inconvenience to the user during treatment. The background technology of the present disclosure is disclosed in Korean Patent Laid-open Publication No. 10-2012-0115739 (published on Oct. 19, 2012).

DISCLOSURE OF THE INVENTION

Problems to be Solved by the Invention

The present disclosure is conceived to solve the above-described problem of the conventional technology and thus provides an inner ear therapy device capable of simultaneously or selectively irradiating a magnetic field and lights of various wavelength ranges, such as a red light, a blue light, and a far infrared light, toward the inner ear and a method for operating the inner ear therapy device.

Further, the present disclosure is conceived to solve the above-described problem of the conventional technology and thus provides an inner ear therapy device which does not require a user to grip with his/her hand for a long time but is wearable in the form of a hearing aid, earphones, or headphones.

However, problems to be solved by the present disclosure are not limited to the above-described problems. There may be other problems to be solved by the present disclosure.

Means for Solving the Problems

As a technical means for solving the above-described technical problem, an inner ear therapy device according to an exemplary embodiment of the present disclosure may include a magnetic field generation unit configured to generate a magnetic field toward the inner ear of a user, multiple light sources configured to irradiate multiple lights having different wavelengths to the inner ear, and a control unit configured to control operations of the magnetic field generation unit and the multiple light sources.

According to an example of the present exemplary embodiment, the control unit may simultaneously operate at least two of the multiple light sources and the magnetic field generation unit.

According to an example of the present exemplary embodiment, the inner ear therapy device further includes an inner ear insertion unit, and the magnetic field generation unit and the multiple light sources may be provided within the inner ear insertion unit.

According to an example of the present exemplary embodiment, the inner ear insertion unit may include: a first protrusion which is to be inserted into the ear; and a second protrusion which is formed symmetrically with the first protrusion and to be inserted into the ear, and the magnetic field generation unit may be provided within the first protrusion and the multiple light sources may be provided within the second protrusion.

According to an example of the present exemplary embodiment, the inner ear therapy device may further include a cable that electrically connects the control unit to the inner ear insertion unit.

According to an example of the present exemplary embodiment, the inner ear insertion unit may be plural in number.

According to an example of the present exemplary embodiment, the inner ear therapy device may further include a cap which is detachable from a front end of the inner ear insertion unit and to be inserted into the inner ear.

According to an example of the present exemplary embodiment, the control unit may alternately operate at least two of the multiple light sources and the magnetic field generation unit according to a predetermined cycle.

According to an example of the present exemplary embodiment, the control unit may operate the magnetic field generation unit in order for the magnetic field generation unit to generate a first magnetic field when a first light source among the multiple light sources is operated and to generate a second magnetic field when a second light source among the multiple light sources is operated, and the first magnetic field and the second magnetic field may be different from each other in any one of a generation time, type, or size.

According to an example of the present exemplary embodiment, the type may include at least any one of a sinewave type, a monophasic type, and a biphasic type.

According to an example of the present exemplary embodiment, the multiple light sources may include a first light source configured to irradiate a first light having a wavelength range of 400 nm; a second light source configured to irradiate a second light having a wavelength range of 660 nm; and a third light source configured to irradiate a far infrared light having a wavelength of at least any one of 2.5 μm to 50 μm.

According to an example of the present exemplary embodiment, the first light may be a blue light and the second light may be a red light.

According to an example of the present exemplary embodiment, the first light source, the second light source, and the third light source may be light emitting diodes (LEDs).

According to an example of the present exemplary embodiment, the magnetic field generation unit may include: a magnetic field core including a magnetic substance and having a dumbbell shape; and a magnetic field coil wound around the magnetic field core.

According to an example of the present exemplary embodiment, a hole may be formed to penetrate the center of the magnetic field core, and the multiple light sources may irradiate multiple lights to the inner ear through the hole.

According to an example of the present exemplary embodiment, the multiple light sources may protrude on a surface of the magnetic field generation unit, and the inner ear therapy device may further include: two headphone bodies that accommodate the magnetic field generation unit; a headphone connecting part configured to connect the two headphone bodies; and a cap which covers the multiple light sources and is to be inserted into the inner ear.

As a technical means for solving the above-described technical problem, a method for operating an inner ear therapy device including a first light source, a second light source, a third light source, and a magnetic field generation unit according to an exemplary embodiment of the present disclosure may include: operating at least any one of the first light source configured to irradiate a first light having a first wavelength toward the inner ear of a user, the second light source configured to irradiate a second light having a second wavelength toward the inner ear, and the third light source configured to irradiate a third light having a third wavelength toward the inner ear together with the magnetic field generation unit configured to generate a magnetic field toward the inner ear.

According to an example of the present exemplary embodiment, the first light may have a wavelength range of 400 nm, the second light may have a wavelength range of 660 nm, and the third light may have a wavelength of at least any one of 2.5 μm to 50 μm.

As a technical means for solving the above-described technical problem, a storage medium according to an exemplary embodiment of the present disclosure may store a program configured to execute a method for operating an inner ear therapy device on a computer, wherein the method for operating an inner ear therapy device includes operating at least any one of a first light source configured to irradiate a first light having a first wavelength toward the inner ear of a user, a second light source configured to irradiate a second light having a second wavelength toward the inner ear, and a third light source configured to irradiate a third light having a third wavelength toward the inner ear together with a magnetic field generation unit configured to generate a magnetic field toward the inner ear.

As a technical means for solving the above-described technical problem, a computer program according to an exemplary embodiment of the present disclosure may be stored in a storage medium in order to execute a method for operating an inner ear therapy device on a computer, wherein the method for operating an inner ear therapy device includes operating at least any one of a first light source configured to irradiate a first light having a first wavelength toward the inner ear of a user, a second light source configured to irradiate a second light having a second wavelength toward the inner ear, and a third light source configured to irradiate a third light having a third wavelength toward the inner ear together with a magnetic field generation unit configured to generate a magnetic field toward the inner ear.

The above-described exemplary embodiments are provided by way of illustration only and should not be construed as liming the present disclosure. Besides the above-described exemplary embodiments, there may be additional exemplary embodiments described in the accompanying drawings and the detailed description.

Effects of the Invention

According to any one of the above-described means for solving the problems, a magnetic field and lights of various wavelength ranges, such as a red light, a blue light, and a far infrared light, are irradiated toward the inner ear, and, thus, the effect of treating inner ear diseases such as middle ear infection can be improved, and a light source or a magnetic field can be selectively irradiated depending on symptoms.

According to any one of the above-described means for solving the problems, while a user wears an inner ear therapy device in the form of a hearing aid, earphones, or headphones, inner ear therapy is conducted, and, thus, the user does not need to grip the therapy device for a long time and may feel less fatigue.

BRIEF DESCRIPTION OF THE DRAWINGS

FIG. 7 is a flowchart showing a method for operating an inner ear therapy device in accordance with an exemplary embodiment of the present disclosure.

BEST MODE FOR CARRYING OUT THE INVENTION

Figure 1:
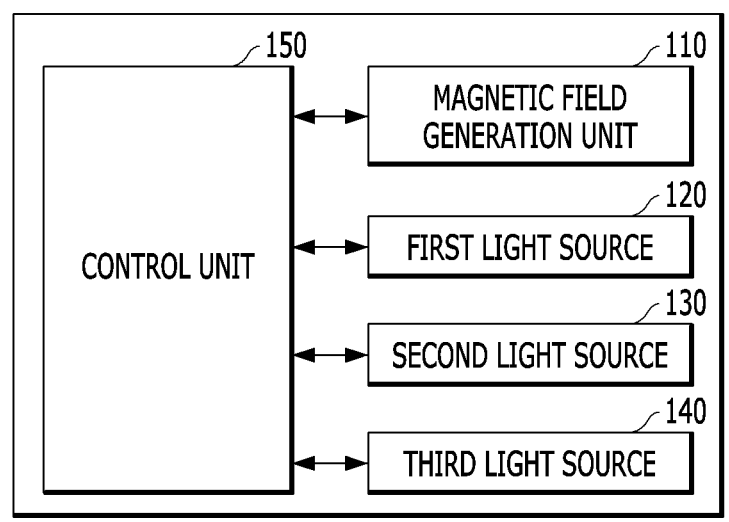
FIG. 1 is a block diagram of an inner ear therapy device in accordance with an exemplary embodiment of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to"

another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

FIG. 1 is a block diagram of an inner ear therapy device in accordance with an exemplary embodiment of the present disclosure. As illustrated in FIG. 1, an inner ear therapy device 100 in accordance with an exemplary embodiment of the present disclosure may include a magnetic field generation unit 110, multiple light sources including a first light source 120, a second light source 130 and a third light source 140, and a control unit 150. However, in some exemplary embodiments of the present disclosure, the inner ear therapy device 100 may have a different configuration from that illustrated in FIG. 1.

The magnetic field generation unit 110 may generate a magnetic field toward the inner ear of a user. For example, magnetic fields generated by the magnetic field generation unit 110 may be pulsed electromagnetic fields (PEMFs). Further, magnetic fields generated by the magnetic field generation unit 110 may be weak magnetic fields having a size of from about 1 Gauss to about 300 Gauss. A magnetic field can increase the activity of blood flow in a human body and facilitate metabolism in which oxygen and nutrients in blood are combined and transported to each cellular tissue and organ. Further, the magnetic field can promote blood circulation and rapidly eliminate waste matters from the body and thus prevent a disease. Furthermore, the magnetic field can promote the ion effect to normalize blood circulation, and also increase the oxygen efficiency to convert body fluid into healthy alkaline body fluid. When the magnetic field is supplied to a human body, the magnetic field affects iron in red blood cells, and, thus, agglutinated red blood cells can be reduced and the action mechanism of blood can be active.

The magnetic field generation unit 110 may generate a magnetic field while at least one of the first light source 120, the second light source 130, and the third light source 140 is operated. For example, the magnetic field generation unit 110 may generate a first magnetic field while the first light source 120 is operated. Further, the magnetic field generation unit 110 may generate a second magnetic field while the second light source 130 is operated. The first magnetic field and the second magnetic field may be different from each other in any one of a generation time, type, or size (intensity). For example, the type of the first magnetic field and the second magnetic field may include at least any one of a sinewave or squarewave (monophasic) type, a biphasic type, or a pulse wave.

The first light source 120 may irradiate a first light having a first wavelength toward the inner ear of the user. For example, the first light may be a blue light, and the first wavelength may be set to a wavelength range of from 400 nm to 415 nm. As another example, the first wavelength of the first light may be selected from a range of from 200 nm to 400 nm. The blue light has a sterilization effect by destroying germs and bacteria.

The second light source 130 may irradiate a second light having a second wavelength toward the inner ear of the user. For example, the second light may be a red light, and the second wavelength may be selected from a range of from 630 nm to 670 nm. The red light has effects of restorative action, wound healing, and analgesic action, and also has effects of wound repair and anti-inflammatory action by inducing the secretion of cytokine that stimulates the generation of growth factor of cells and the proliferation of fibroblast.

The third light source 140 may irradiate a third light having a third wavelength toward the inner ear of the user. For example, the third light may be a far infrared light, and the third wavelength may be selected from a range of from 2.5 μm to 50 μm.

According to an exemplary embodiment of the present disclosure, the first light source 120, the second light source 130, and the third light source 140 may alternately irradiate the first light, the second light, and the third light toward the inner ear according to a predetermined cycle. For example, after the first light source 120 irradiates the first light toward the inner ear of the user for 30 seconds and the irradiation of the first light is completed, the second light source 130 may irradiate the second light toward the inner ear of the user for 30 seconds, and when the irradiation of the second light is completed, the third light source 140 may irradiate the third light toward the inner ear of the user for 30 seconds. Further, according to another exemplary embodiment of the present disclosure, at least two of the first light source 120, the second light source 130, and the third light source 140 may simultaneously irradiate lights.

Further, the first light source 120, the second light source 130, and the third light source 140 may include light emitting diodes (LEDs). A LED is more durable and smaller in size than a laser. Further, a medical LED does not require a high voltage and generates less heat and thus is suitable for brachytherapy. Furthermore, the LED can emit a light of a broad wavelength range and has a small wavelength width, and, thus, it is easy to select a wavelength required for therapy.

The control unit 150 may control operations of the magnetic field generation unit 110 and the multiple light sources including the first light source 120, the second light source 130, and the third light source 140. For example, the control unit 150 may generate a control signal for controlling the operations of the magnetic field generation unit 110, the first light source 120, the second light source 130, and the third light source 140 and transmit the control signal to the magnetic field generation unit 110, the first light source 120, the second light source 130, and the third light source 140.

According to an exemplary embodiment of the present disclosure, the control unit 150 may generate a control signal in consideration of the correlation between at least two of the magnetic field generation unit 110, the first light source 120, the second light source 130, and the third light source 140. For example, the control unit 150 may generate a control signal for operating the magnetic field generation unit 110 while at least one of the first light source 120, the second light source 130, and the third light source 140 is operated. As another example, the control unit 150 may generate a control signal for alternately operating the magnetic field generation unit 110, the first light source 120, the second light source 130, and the third light source 140 according to a predetermined cycle. As yet another example, the control unit 150 may generate a control signal for controlling the magnetic field generation unit 110 to generate a first magnetic field corresponding to the first light source 120 while the first light source 120 is operated. Also, the control unit 150 may generate a control signal for controlling the magnetic field generation unit 110 to generate a second magnetic field corresponding to the second light source 130 while the second light source 130 is operated.

The control unit 150 may generate an electric signal or control signal for controlling the operations of the magnetic field generation unit 110, the first light source 120, the second light source 130, and the third light source 140 on the basis of the user's input for selecting an intensity or duration time of a magnetic field and the user's input for selecting the kind of a light source, a wavelength range, or a duration time received from a user input unit which is not illustrated in FIG. 1.

As described above, in the inner ear therapy device 100 according to an exemplary embodiment of the present disclosure, the first light, the second light, and the third light of different wavelength ranges and a magnetic field are simultaneously or selectively irradiated toward the inner ear of the user depending on symptoms of an inner ear disease, and, thus, it is possible to maximize the effect of treating inner ear diseases such as middle ear infection or external ear infection.

Figure 2:
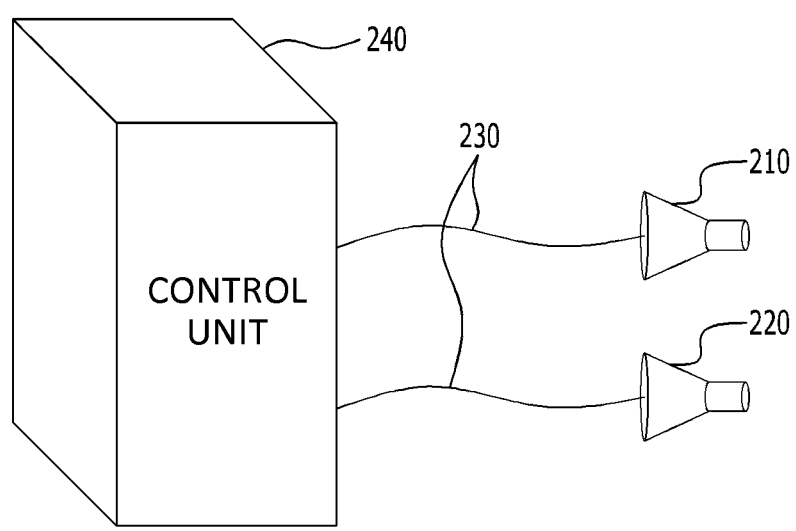
FIG. 2 is a configuration diagram of an inner ear therapy device in accordance with an exemplary embodiment of the present disclosure.

FIG. 2 is a configuration diagram of an inner ear therapy device in accordance with an exemplary embodiment of the present disclosure. As illustrated in FIG. 2, an inner ear therapy device 200 in accordance with an exemplary embodiment of the present disclosure may include a first inner ear insertion unit 210, a second inner ear insertion unit 220, a cable 230, and a control unit 240.

In each of the first inner ear insertion unit 210 and the second inner ear insertion unit 220, a magnetic field generation unit configured to generate a magnetic field toward the inner ear of a user and multiple light sources configured to irradiate multiple lights respectively having different wavelengths toward the inner ear may be provided. The magnetic field generation unit and the multiple light sources have been described above in detail with reference to FIG. 1, and, thus, a detailed explanation thereof will be omitted. Front ends of the first inner ear insertion unit 210 and the second inner ear insertion unit 220 protrude corresponding to an average human earhole size and thus can be easily inserted into the inner ear of the user.

The cable 230 may electrically connect the first inner ear insertion unit 210 and the second inner ear insertion unit 220 to the control unit 240. The magnetic field generation unit and the multiple light sources provided within the first inner ear insertion unit 210 and the second inner ear insertion unit 220 may receive a control signal from the control unit 240 through the cable 230. However, according to another exemplary embodiment of the present disclosure, the cable 230 can be omitted, and the first inner ear insertion unit 210 and the second inner ear insertion unit 220 may be connected to the control unit 240 through a wireless communication network such as Bluetooth.

The control unit 240 may perform the function of the control unit 150 of the inner ear therapy device 100 illustrated in FIG. 1 in the same manner. Further, although not illustrated in FIG. 2, the control unit 240 may include an interface configured to receive the user's input for selecting a magnetic field intensity or operation time of the magnetic field generation units included in the first inner ear insertion unit 210 and the second inner ear insertion unit 220. Further, the control unit 240 may include an interface configured to receive the user's input for selecting a wavelength range or operation time of the multiple light sources included in the first inner ear insertion unit 210 and the second inner ear insertion unit 220. For example, the control unit 240 may include a separate switch, a button, a touch panel display, and a motion recognition unit for controlling power supply to the inner ear therapy device 200 or selecting a magnetic field intensity, an operation time, a wavelength range of a light source, but is not necessarily limited thereto.

Further, the control unit 240 can be moved as being carried by a person, attached to a wall, or installed in a cart. Although FIG. 2 illustrates that the two inner ear insertion units 210 and 220 are connected to the control unit 240, the control unit 240 may be connected to an inner ear insertion unit or three or more inner ear insertion units.

Figure 3A:
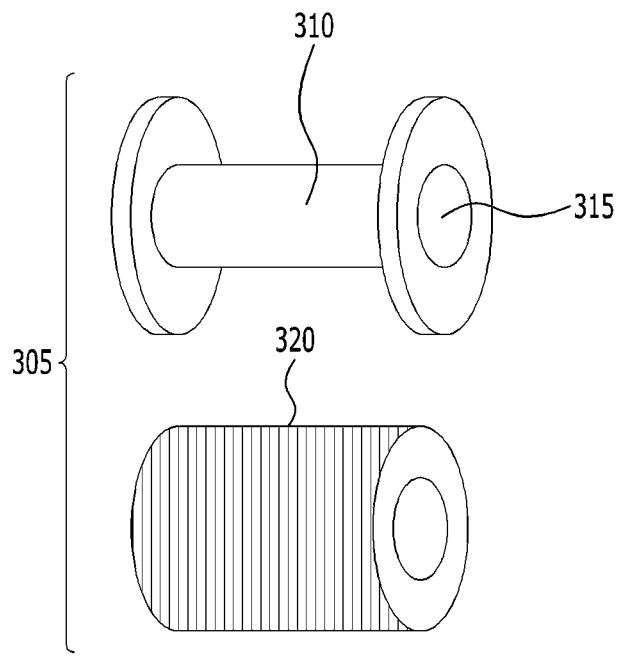
FIG. 3A illustrates an exemplary magnetic field generation unit of an inner ear therapy device in accordance with an exemplary embodiment of the present disclosure.

FIG. 3A illustrates an exemplary magnetic field generation unit of an inner ear therapy device in accordance with an exemplary embodiment of the present disclosure. As illustrated in FIG. 3A, a magnetic field generation unit 305 of an inner ear therapy device in accordance with an exemplary embodiment of the present disclosure may include a magnetic field core 310 and a magnetic field coil 320 wound around the magnetic field core 310.

For example, the magnetic field core 310 may include a magnetic substance and may have a dumbbell shape. For example, the diameter of the magnetic substance can be selected from a range of from 2 mm to 5 mm. Further, the magnetic substance may be formed of a material such as SM45C. Further, as illustrated in FIG. 3A, a hole 315 may be formed to penetrate the center of the dumbbell-shaped magnetic field core 310.

When an alternating current is applied to the magnetic field generation unit 305 by power supplied to the inner ear therapy device, a time-varying magnetic field is generated by the magnetic field core 310 including the magnetic substance and the magnetic field coil 320 wound around the magnetic field core 310. Herein, the generated magnetic field may be Pulsed Electromagnetic Fields Stimulation (PEMFs). The time-varying magnetic field may cause the generation of bioelectric currents, and cells in an affected part may be stimulated by the bioelectric currents, and, thus, treatment for the inner ear disease and recovery can be accelerated. An intensity of a magnetic field generated by the magnetic field generation unit 305 can be controlled in a range of from 100 Gauss to 300 Gauss depending on a size of the magnetic substance and the number of winding of coil 320 in the magnetic field generation unit 305.

Figure 3B:
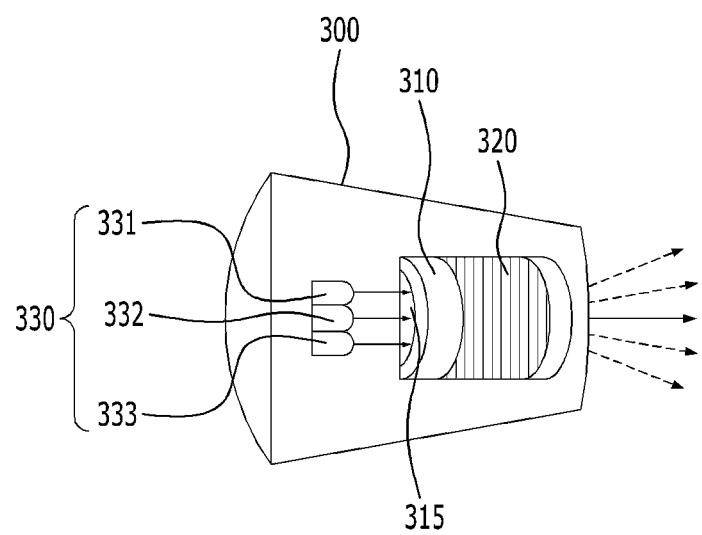
FIG. 3B illustrates a cross-section of an inner ear insertion unit of an inner ear therapy device in accordance with an exemplary embodiment of the present disclosure.

FIG. 3B illustrates a cross-section of an inner ear insertion unit of an inner ear therapy device in accordance with an exemplary embodiment of the present disclosure. As illustrated in FIG. 3B, according to an exemplary embodiment of the present disclosure, an inner ear insertion unit 300 may include a magnetic field generation unit including the magnetic field core 310 and the magnetic field coil 320 and multiple light sources 330 including a first light source 331, a second light source 332, and a third light source 333 configured to irradiate lights having different wavelengths, respectively. For example, as illustrated in FIG. 3B, the magnetic field generation unit may be positioned in a protrusion part of the inner ear insertion unit 300 and the multiple light sources 330 may be positioned in back of the magnetic field generation unit. Further, the multiple light sources 330 may irradiate lights toward the inner ear of the user through the hole 315 formed to penetrate the center of the magnetic field core 310.

Figure 3C:
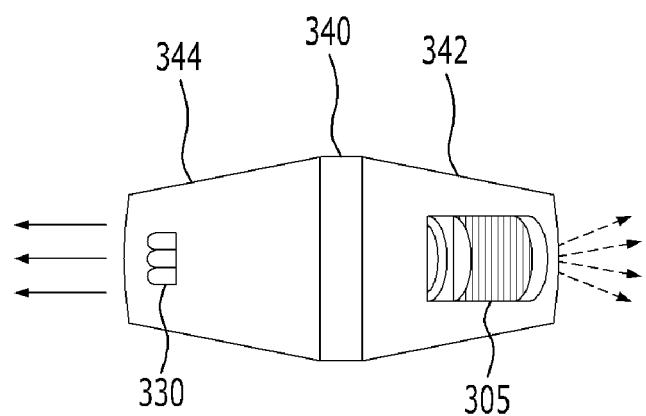
FIG. 3C illustrates a cross-section of an inner ear insertion unit of an inner ear therapy device in accordance with another exemplary embodiment of the present disclosure.

FIG. 3C illustrates a cross-section of an inner ear insertion unit of an inner ear therapy device in accordance with another exemplary embodiment of the present disclosure. As illustrated in FIG. 3C, according to another exemplary embodiment of the present disclosure, an inner ear insertion unit 340 may include a first protrusion 342 which is to be inserted into the inner ear and a second protrusion 344 which is formed symmetrically with the first protrusion 342 and to be inserted into the inner ear.

Further, the magnetic field generation unit 305 may be provided within the first protrusion 342 of the inner ear insertion unit 340 and the multiple light sources 330 may be provided within the second protrusion 344. Therefore, when the user wants to irradiate a magnetic field or light toward the inner ear, a protrusion including the magnetic field generation unit or the light sources therein may be selected and inserted into the inner ear.

Figure 4:
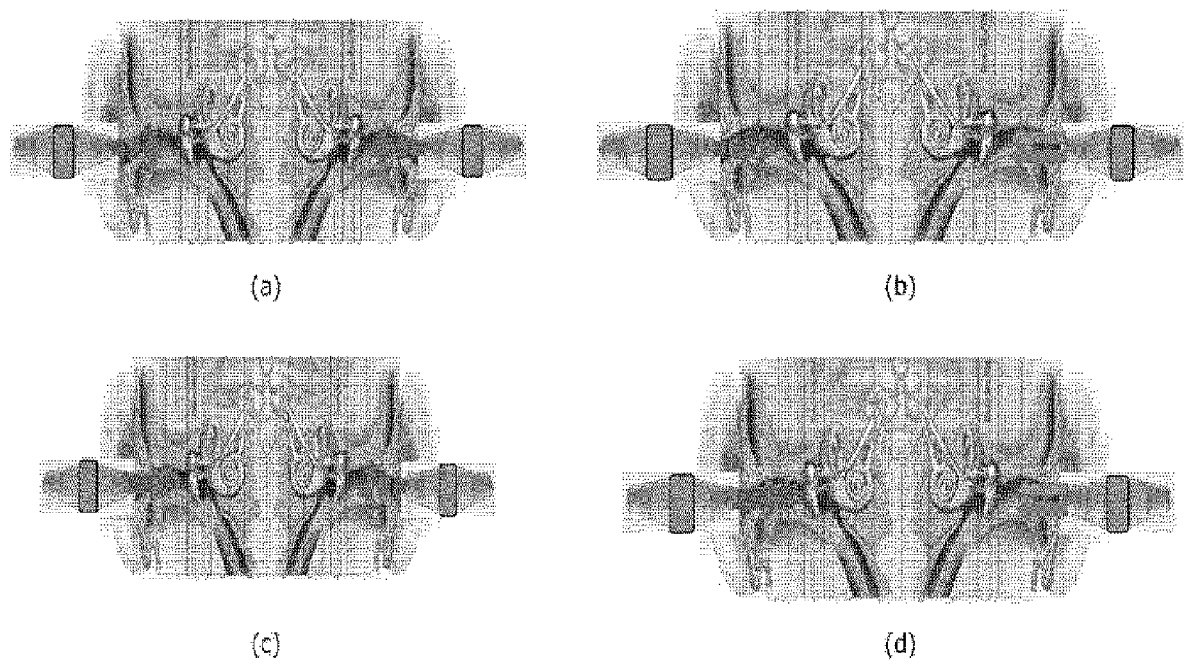
FIG. 4 is diagrams illustrating an operation of an inner ear therapy device in accordance with an exemplary embodiment of the present disclosure.

FIG. 4 is diagrams illustrating an operation of the inner ear therapy device in accordance with an exemplary embodiment of the present disclosure. As illustrated in (a) to (d) of FIG. 4, according to the present disclosure, the user may treat an inner ear disease by simultaneously operating at least two of a magnetic field generation unit and multiple light sources depending on the kind, symptoms, or the severity of the inner ear disease. For example, as illustrated in (a) of FIG. 4, the user may insert two inner ear insertion units into both ears, respectively, and operate magnetic field generation units included in the respective inner ear insertion units to irradiate magnetic fields toward the inner ears. In another example, as illustrated in (b) of FIG. 4, the user may insert two inner ear insertion units into both ears, respectively, and operate a magnetic field generation unit included in one of the inner ear insertion units to irradiate a magnetic field into the corresponding inner ear and simultaneously or alternately operate a first light source and a second light source included in the other inner ear insertion unit to irradiate a blue light and a red light toward the corresponding inner ear. In yet another example, as illustrated in (c) of FIG. 4, the user may insert two inner ear insertion units into both ears, respectively, and operate a third light source included in one of the inner ear insertion units to irradiate a far infrared light into the corresponding inner ear and operate a magnetic field generation unit included in the other inner ear insertion unit to irradiate a magnetic field toward the inner ear. In still another example, as illustrated in (d) of FIG. 4, the user may insert two inner ear insertion units into both ears, respectively, and operate a first light source included in one of the inner ear insertion units to irradiate a far infrared light into the corresponding inner ear and simultaneously or alternately operate a second light source and a third light source included in the other inner ear insertion unit to irradiate a blue light and a red light toward the corresponding inner ear.

Figure 5A:
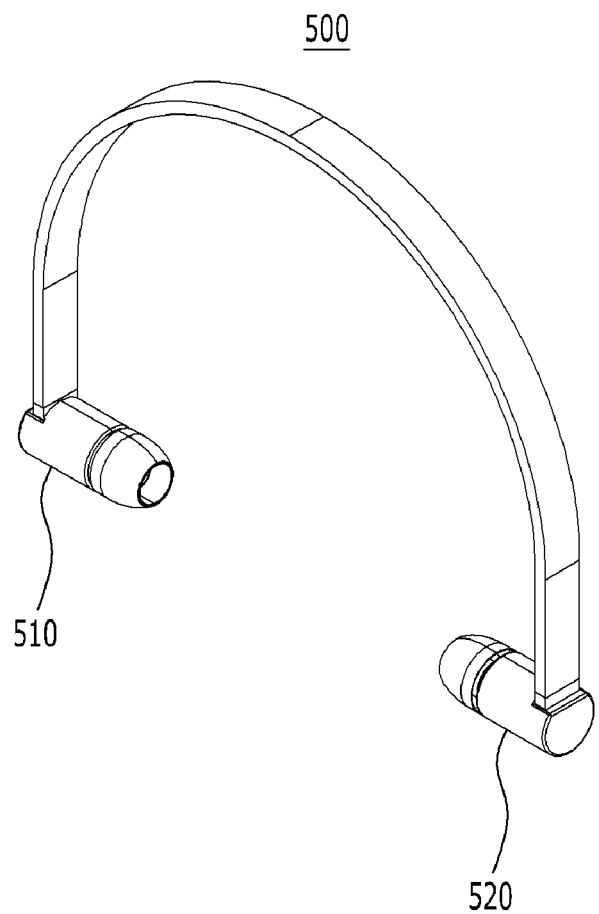
FIG. 5A to FIG. 5E are configuration diagrams of an inner ear therapy device in accordance with another exemplary embodiment of the present disclosure.
Figure 5B:
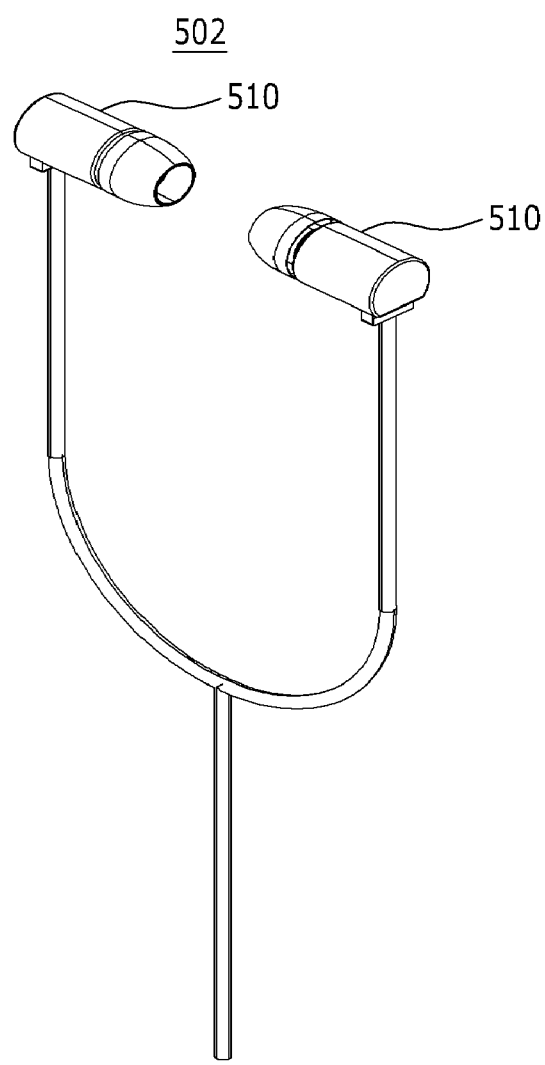

FIG. 5A to FIG. 5E are configuration diagrams of an inner ear therapy device in accordance with another exemplary embodiment of the present disclosure. As illustrated in FIG. 5A, an inner ear therapy device 500 in accordance with an exemplary embodiment of the present disclosure may include multiple inner ear insertion units 510 and 520 and may be configured as earphones. Further, as illustrated in FIG. 5B, an inner ear therapy device 502 in accordance with another exemplary embodiment of the present disclosure may include multiple inner ear insertion units 510 and 520 and may be configured as a stethoscope. According to the present disclosure, the user does not need to grip the inner ear therapy device 500 or 502 with his/her hand during treatment for an inner ear disease and can wear the inner ear therapy device 500 or 502 without a separate fixing device. Therefore, the user's inconvenience can be reduced.

Figure 5C:
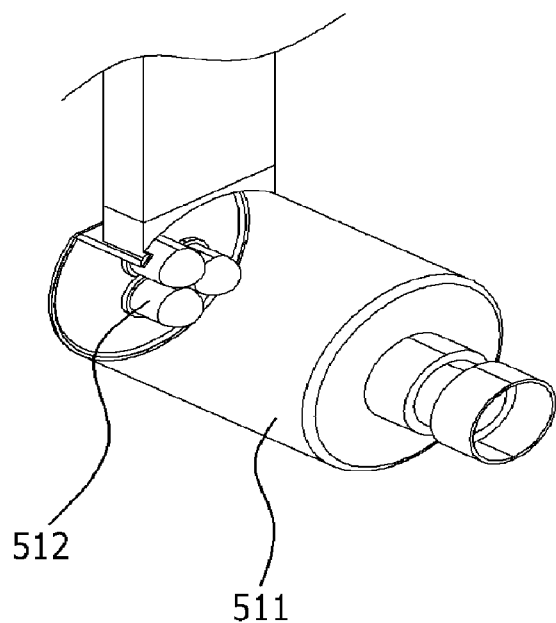
Figure 5D:
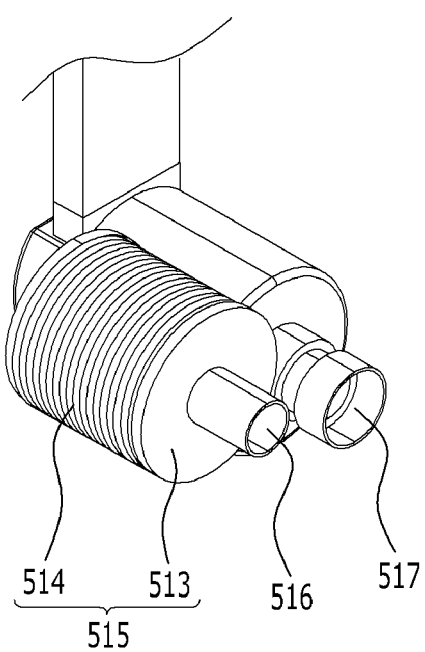
Figure 5E:
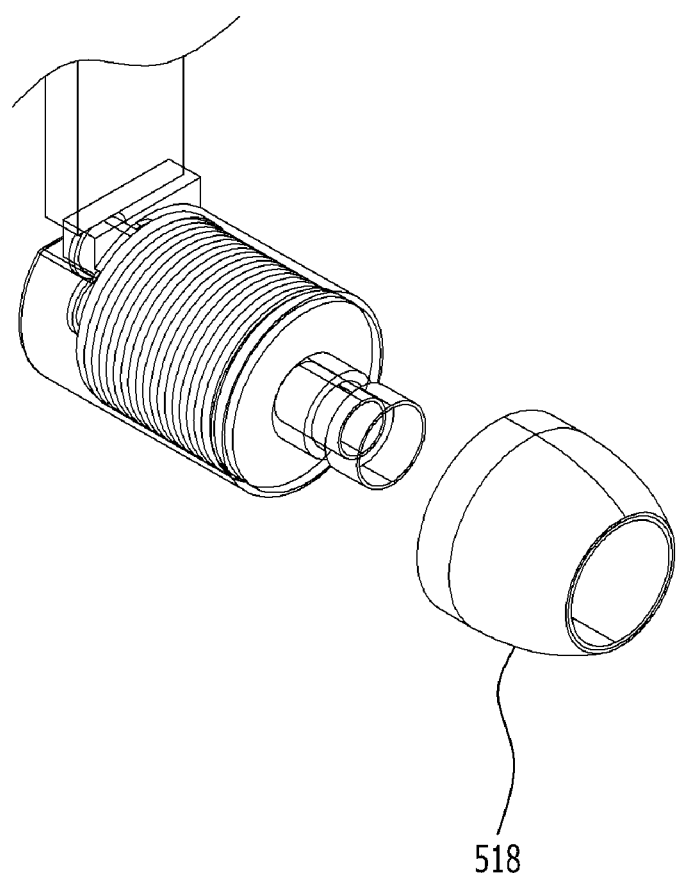

Further, as illustrated in FIG. 5C to FIG. 5E, an inner ear insertion unit according to an exemplary embodiment of the present disclosure may include a housing 511, multiple light sources 512 accommodated in the housing 511, and a magnetic field generation unit 515 including a magnetic field core 513 and a magnetic field coil 514. A hole 516 may be formed to penetrate the center of the magnetic field core 513, and a hole 517 may also be formed at the center of a front end of the housing 511. Therefore, the multiple light sources 512 and the magnetic field generation unit 515 may be accommodated in the housing 511, and, thus, a light and a magnetic field can be irradiated to the inner ear through the hole 516 of the magnetic field core 513 and the hole 517 of the housing 511.

Further, as illustrated in FIG. 5E, the inner ear therapy device according to an exemplary embodiment of the present disclosure may include a cap 518 which is detachable from a front end of an inner ear insertion unit and to be inserted into the inner ear. For example, the cap 518 may be formed of silicon, plastic, or vinyl. Therefore, the user can more easily insert the inner ear insertion units of the inner ear therapy device into the inner ear and more sanitarily use the inner ear therapy device.

Figure 6A:
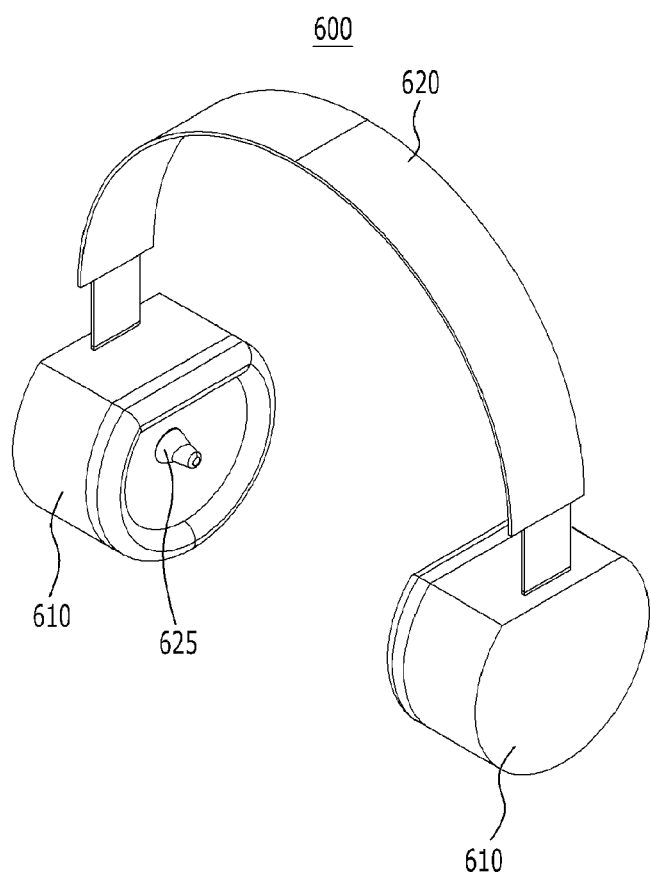
FIG. 6A to FIG. 6C are configuration diagrams of an inner ear therapy device in accordance with yet another exemplary embodiment of the present disclosure.
Figure 6B:
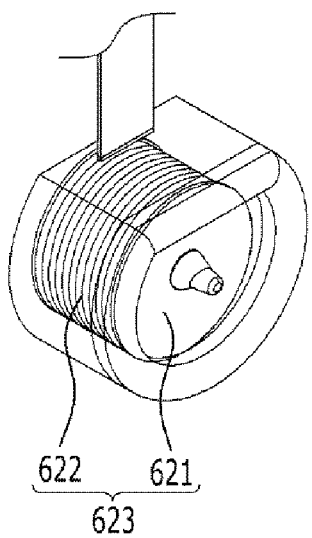
Figure 6C:
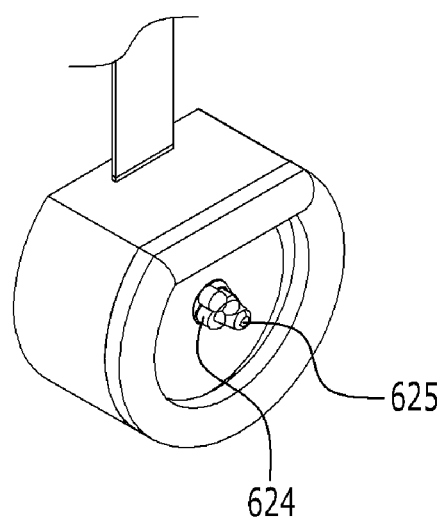

FIG. 6A to FIG. 6C are configuration diagrams of an inner ear therapy device in accordance with yet another exemplary embodiment of the present disclosure. As illustrated in FIG. 6A to FIG. 6C, an inner ear therapy device 600 in accordance with another exemplary embodiment of the present disclosure may be configured as headphones including multiple headphone bodies 610 and a headphone connecting part 620 configured to connect the multiple headphone bodies 610.

According to an exemplary embodiment of the present disclosure, each of the headphone bodies 610 may accommodate a magnetic field generation unit 623 including a dumbbell-shaped magnetic field core 621 including a magnetic substance and a magnetic field coil 622 wound around the magnetic field core 621. Further, multiple light sources 624 may protrude on a surface of the magnetic field core 621 of the magnetic field generation unit 623. Furthermore, a cap 625 which covers the multiple light sources 624 and is to be inserted into the inner ear may be attached to and detached from the surface of the magnetic field core 621. For example, the cap 625 may be formed of silicon, plastic, or vinyl.

FIG. 7 is a flowchart showing a method for operating an inner ear therapy device in accordance with an exemplary embodiment of the present disclosure. The method for operating an inner ear therapy device illustrated in FIG. 7 is performed by the inner ear therapy device described above with reference to FIG. 1 to FIG. 6C. Therefore, descriptions of the inner ear therapy device illustrated in FIG. 1 to FIG. 6C may be identically applied to the method for operating an inner ear therapy device illustrated in FIG. 7, even though they are omitted hereinafter.

In S710, a control unit (control device) generates a control signal. In S720, the control unit operates at least one of a first light source, a second light source, and a third light source on the basis of the control signal. The first light source may irradiate a first light having a first wavelength toward the inner ear of the user, the second light source may irradiate a second light having a second wavelength toward the inner ear of the user, and the third light source may irradiate a third light having a third wavelength toward the inner ear of the user. In S730, the control unit may operate a magnetic field generation unit to generate a magnetic field toward the inner ear on the basis of the control signal while at least one of the first light source, the second light source, and the third light source is operated.

The above-described method for operating the inner ear therapy device can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

Further, the above-described method for operating the inner ear therapy device can be embodied in a computer program to be stored in a storage medium.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An inner ear therapy device comprising:
   a magnetic field generation unit configured to generate a magnetic field toward the inner ear of a user;
   multiple light sources configured to irradiate multiple lights having different wavelengths to the inner ear; and
   a control unit configured to control operations of the magnetic field generation unit and the multiple light sources.

2. The inner ear therapy device of claim 1,
   wherein the control unit simultaneously operates at least two of the multiple light sources and the magnetic field generation unit.

3. The inner ear therapy device of claim 1, further comprising:
   an inner ear insertion unit,
   wherein the magnetic field generation unit and the multiple light sources are provided within the inner ear insertion unit.

4. The inner ear therapy device of claim 3,
   wherein the inner ear insertion unit includes:
   a first protrusion which is to be inserted into the ear; and
   a second protrusion which is formed symmetrically with the first protrusion and to be inserted into the ear, and
   the magnetic field generation unit is provided within the first protrusion and the multiple light sources are provided within the second protrusion.

5. The inner ear therapy device of claim 4, further comprising:
   a cable that electrically connects the control unit to the inner ear insertion unit.

6. The inner ear therapy device of claim 3,
   wherein the inner ear insertion unit is plural in number.

7. The inner ear therapy device of claim 3, further comprising:
   a cap which is detachable from a front end of the inner ear insertion unit and to be inserted into the inner ear.

8. The inner ear therapy device of claim 1,
   wherein the control unit alternately operates at least two of the multiple light sources and the magnetic field generation unit according to a predetermined cycle.

9. The inner ear therapy device of claim 1,
   wherein the control unit operates the magnetic field generation unit in order for the magnetic field generation unit to generate a first magnetic field when a first light source among the multiple light sources is operated and to generate a second magnetic field when a second light source among the multiple light sources is operated, and
   the first magnetic field and the second magnetic field are different from each other in any one of a generation time, type, or size.

10. The inner ear therapy device of claim 9,
    wherein the type includes at least any one of a sinewave type, a monophasic type, and a biphasic type.

11. The inner ear therapy device of claim 1,
    wherein the multiple light sources include:
    a first light source configured to irradiate a first light having a wavelength range of 400 nm;
    a second light source configured to irradiate a second light having a wavelength range of 660 nm; and
    a third light source configured to irradiate a far infrared light having a wavelength of at least any one of 2.5 μm to 50 μm.

12. The inner ear therapy device of claim 11,
    wherein the first light is a blue light and the second light is a red light.

13. The inner ear therapy device of claim 11,
    wherein the first light source, the second light source, and the third light source are light emitting diodes (LEDs).

14. The inner ear therapy device of claim 1,
    wherein the magnetic field generation unit includes:
    a magnetic field core including a magnetic substance and having a dumbbell shape; and
    a magnetic field coil wound around the magnetic field core.

15. The inner ear therapy device of claim 14,
    wherein a hole is formed to penetrate the center of the magnetic field core, and
    the multiple light sources irradiate multiple lights to the inner ear through the hole.

16. The inner ear therapy device of claim 14,
    wherein multiple light sources protrude on a surface of the magnetic field generation unit, and
    the inner ear therapy device further comprises:
    two headphone bodies that accommodate the magnetic field generation unit;

a headphone connecting part configured to connect the two headphone bodies; and a cap which covers the multiple light sources and is to be inserted into the inner ear.

17. A method for operating an inner ear therapy device including a first light source, a second light source, a third light source, and a magnetic field generation unit, the method comprising:

operating at least any one of the first light source configured to irradiate a first light having a first wavelength toward the inner ear of a user, the second light source configured to irradiate a second light having a second wavelength toward the inner ear, and the third light source configured to irradiate a third light having a third wavelength toward the inner ear together with the magnetic field generation unit configured to generate a magnetic field toward the inner ear.

18. The method for operating an inner ear therapy device of claim 17, wherein the first light has a wavelength range of 400 nm, the second light has a wavelength range of 660 nm, and the third light has a wavelength of at least any one of 2.5 μm to 50 μm.

19. A non-transitory storage medium that stores a program configured to execute the method of claim 17 on a computer.

* * * * *